(12) United States Patent
Morman et al.

(10) Patent No.: US 6,465,073 B1
(45) Date of Patent: Oct. 15, 2002

(54) VARIABLE STRETCH MATERIAL AND PROCESS TO MAKE IT

(75) Inventors: Michael Tod Morman, Alpharetta, GA (US); Thomas Walter Odorzynski, Green Bay; Georgia Lynn Zehner, Larsen, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/346,665

(22) Filed: Jun. 30, 1999

(51) Int. Cl.$^7$ .............................. B32B 3/00; B32B 27/14; B32B 5/26; D04H 1/00

(52) U.S. Cl. .................. 428/103; 428/195; 428/198; 442/328; 442/381; 442/394

(58) Field of Search ................... 442/328, 381, 442/394; 428/103, 195, 198

(56) References Cited

U.S. PATENT DOCUMENTS

| | | | |
|---|---|---|---|
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,949,128 A | 4/1976 | Ostermeier | 428/152 |
| 4,100,324 A | 7/1978 | Anderson et al. | 428/288 |
| 4,296,163 A | 10/1981 | Emi et al. | 428/212 |
| 4,340,563 A | 7/1982 | Appel et al. | 264/518 |
| 4,443,513 A | 4/1984 | Meitner et al. | 422/195 |
| 4,507,163 A | 3/1985 | Menard | 156/164 |
| 4,525,407 A | 6/1985 | Ness | 428/138 |
| 4,652,487 A | 3/1987 | Morman | 428/138 |
| 4,657,802 A | 4/1987 | Morman | 428/152 |
| 4,720,415 A | 1/1988 | Vander Wielen et al. | 428/152 |
| 4,781,966 A | 11/1988 | Taylor | 428/152 |
| 4,789,699 A | 12/1988 | Kieffer et al. | 524/271 |
| 4,834,741 A * | 5/1989 | Sabee | 604/385.2 |
| 4,863,779 A | 9/1989 | Daponte | 428/152 |
| 4,935,287 A | 6/1990 | Johnson et al. | 428/198 |
| 4,965,122 A | 10/1990 | Morman | 428/225 |
| 4,981,747 A | 1/1991 | Morman | 428/198 |
| 5,032,122 A | 7/1991 | Noel et al. | 604/391 |

(List continued on next page.)

FOREIGN PATENT DOCUMENTS

| | | | |
|---|---|---|---|
| EP | 552 340 | 7/1993 | A61F/13/15 |
| EP | 552 345 | 7/1993 | A61F/13/15 |
| EP | 582 569 | 2/1994 | B32B/5/26 |
| EP | 602 613 | 6/1994 | D04H/1/56 |
| EP | 603 497 | 6/1994 | D04H/13/00 |
| EP | 604 731 | 7/1994 | B32B/31/00 |
| EP | 646 062 | 4/1995 | B32B/25/08 |
| EP | 662 811 | 7/1995 | A61F/13/15 |
| EP | 707 106 | 4/1996 | D04H/13/00 |
| EP | 713 546 | 5/1996 | D04H/13/00 |
| EP | 788 874 | 8/1997 | B32B/5/24 |
| EP | 803 602 | 10/1997 | D04H/3/16 |
| EP | 820 747 | 1/1998 | A61F/13/15 |
| EP | 863 240 | 9/1998 | D04H/13/00 |
| WO | 98/05813 | 2/1998 | D04H/13/00 |

*Primary Examiner*—Terrel Morris
*Assistant Examiner*—Christopher C. Pratt
(74) *Attorney, Agent, or Firm*—Pauley Petersen Kinne & Erickson (57) ABSTRACT

A stretchable nonwoven web, or laminate of a stretchable nonwoven web and an elastic sheet, is treated with a plurality of bond lines in one or more regions thereof to provide controlled stretching properties. In one embodiment, the nonwoven web or laminate has at least one first region having a plurality of bond lines in a direction parallel to the machine direction and at least one second region having a plurality of bond lines in a direction parallel to the cross-machine direction to provide controlled stretching in different directions in different regions of the web. The bond lines can be substantially continuous in length, or segmented. When segmented bond lines are employed, the length of the bond line segments and spacing between them can be varied to import variable stretch properties to the nonwoven web or laminate.

23 Claims, 4 Drawing Sheets

U.S. PATENT DOCUMENTS

| | | | |
|---|---|---|---|
| 5,114,781 A | 5/1992 | Morman | 428/198 |
| 5,116,662 A | 5/1992 | Morman | 428/198 |
| 5,336,545 A * | 8/1994 | Morman | 428/152 |
| 5,382,461 A | 1/1995 | Wu | 428/86 |
| 5,393,599 A | 2/1995 | Quantrille et al. | 428/284 |
| 5,422,172 A | 6/1995 | Wu | 428/230 |
| 5,494,736 A | 2/1996 | Willey et al. | 428/288 |
| 5,503,908 A | 4/1996 | Faass | 428/198 |
| 5,529,830 A | 6/1996 | Dutta et al. | 428/176 |
| 5,540,976 A | 7/1996 | Shawver et al. | 428/198 |
| 5,592,690 A | 1/1997 | Wu | 2/67 |
| 5,634,216 A | 6/1997 | Wu | 2/239 |
| 5,681,645 A | 10/1997 | Strack et al. | 428/196 |
| 5,709,921 A | 1/1998 | Shawver | 428/152 |
| 5,733,822 A | 3/1998 | Gessner et al. | 442/35 |
| 5,789,065 A | 8/1998 | Haffner et al. | 428/152 |
| 5,804,011 A | 9/1998 | Dutta et al. | 156/160 |
| 5,804,021 A | 9/1998 | Abuto et al. | 156/252 |
| 5,804,286 A | 9/1998 | Quantrille et al. | 428/198 |
| 5,807,292 A | 9/1998 | Delmore | 602/8 |
| 5,814,178 A | 9/1998 | Jacobs | 156/290 |
| 5,824,004 A | 10/1998 | Osborn, III et al. | 604/385.2 |
| 5,837,352 A | 11/1998 | English et al. | 428/198 |
| 5,840,412 A | 11/1998 | Wood et al. | 428/284 |
| 5,843,057 A | 12/1998 | McCormack | 604/367 |
| 5,846,232 A | 12/1998 | Serbiak et al. | 604/385.2 |
| 5,851,935 A | 12/1998 | Srinivasan et al. | 442/328 |
| 5,853,881 A | 12/1998 | Estey et al. | 428/373 |
| 5,861,074 A | 1/1999 | Wu | 156/229 |
| 5,883,028 A | 3/1999 | Morman et al. | 442/394 |
| 5,964,742 A | 10/1999 | McCormack et al. | |
| 6,001,460 A * | 12/1999 | Morman et al. | 428/195 |
| 6,093,665 A | 7/2000 | Sayovitz et al. | |

* cited by examiner

VARIABLE STRETCH MATERIAL AND PROCESS TO MAKE IT

FIELD OF THE INVENTION

This invention is directed to a stretchable nonwoven web or laminate material having bond lines to controllably reduce the stretchability of the web or laminate material in the machine direction and/or the cross-machine direction, and/or in different regions or zones of the material. In one embodiment, this invention is directed to a necked spunbond laminate material having zones or regions stretchable primarily in the machine direction and/or zones or regions stretchable primarily in the cross-machine direction. In another embodiment, the invention is directed to an elastomeric nonwoven web having controlled stretching in one or more directions and/or zones.

BACKGROUND OF THE INVENTION

Many types of elastic webs and processes by which these webs are made are well known in the art. These webs have been used in many personal care absorbent articles because the materials are capable of stretching in more than one direction due to the elasticity of the filaments. Also well known in the art are various types of composite elastic materials having at least one elastic sheet and at least one necked material joined to the elastic sheet, and the processes by which these composite materials are made. These composite elastic materials have also been used in many personal care absorbent articles.

Because the stretchability of the materials is not locally controllable, the materials do not have a predetermined stretch profile, or a predetermined variable stretch. Additionally, these materials do not have regions that stretch only in one direction and other regions in the material that stretch only in another, different direction.

It is often desirable when designing and making new stretchable products including diapers, garments, and workwear to have a material that: (a) has a predetermined stretch profile; (b) is stretchable only in one direction in one region of the material and stretchable only in a different direction in another region of the material; (c) is highly stretchable in one region of the material and stretchable to a lesser extent, but in the same direction, in another region of the material; or (d) exhibits properties of (a), (b) and/or (c) in combination.

SUMMARY OF THE INVENTION

This invention is directed to a stretchable nonwoven web or laminate material useful for personal care products, which has a predetermined and controlled stretch profile. Bond lines are applied in select regions of the material to reduce and, thereby, control the stretchability in directions parallel to the bond lines, in regions where the bond lines exist.

The stretchable nonwoven web of this invention may be a fibrous material such as, for example a spunbond web, a meltblown web, bonded carded web, or a combination thereof. The material may be made of an elastomeric fiber forming polymer. A meltblown web used in this invention may initially be produced using conventional meltblowing processes and apparatus as known in the art whereby a cohesive web is formed. A spunbond web used in this invention may initially be formed by techniques also well known in the art and described in U.S. Pat. No. 4,340,563 to Appel et al.; U.S. Pat. No. 3,692,618 to Dorschner et al.; and U.S. Pat. No. 3,802,817 to Matsuki et al.

A laminate material of this invention may include at least one elastic film or foam layer and a stretchable nonwoven web such as a necked nonwoven web. The nonwoven web is preferably a spunbond web, or a laminate which includes a spunbond web. The nonwoven web is stretched or elongated in a machine direction producing necking of the web in the cross-machine direction. While in an elongated or necked position, the web is bonded to an elastic sheet to form a nonwoven laminate material that is stretchable in a direction parallel to the direction of necking of the web, and which partly or fully recovers when the stretching force is removed. The necked nonwoven web is thermally bonded to the elastic film layer. Other bonding processes may also be used including, but not limited to, adhesive bonding and ultrasonic welding.

In accordance with this invention, bond lines are formed in one or more selected regions of the stretchable nonwoven web or laminate material in one or more selected directions, whereby the stretchability in the selected direction of the material can be controlled and substantially reduced in the region(s) of the bond lines. For example, a material with an initial stretch of about 200% in the cross-machine direction can be reduced to about 100% stretch with cross-machine direction bond lines that cover 50% of the material width.

A bonding strategy can be employed whereby the percentage of the material's area or width occupied by bond lines oriented in one direction is varied to produce a nonwoven web or laminate material which exhibits profiled stretching. This variable bonding can produce a range of elastic elongations in different regions of the same material. Also, the direction of the bond lines can be varied in different regions of the same material, causing different regions to have controlled stretchability in different directions.

In another embodiment of this invention, a stretchable spunbond elastic nonwoven web or necked spunbond laminate comprising an elastic film or foam layer and an elastic spunbond web is provided. The material is initially capable of stretching in the machine direction and in the cross-machine direction. Bond lines can be applied to the elastic nonwoven web or laminate material to produce a material having zoned stretching. Regions of the material contain zones in which bond lines are applied in a direction parallel to the cross-machine direction and zones in which bond lines are applied in a direction nonparallel (preferably perpendicular) to the cross-machine direction, i.e. in the machine direction.

A tensioning force applied in the cross-machine direction to the elastic nonwoven web or elastic laminate material will cause the regions which have bond lines with machine direction orientation to controllably stretch while regions which have bond lines with a cross-machine direction orientation will not stretch or exhibit reduced stretching. Conversely, when a tensioning force is applied in the machine direction to the elastic material, the regions which have bond lines with machine orientation will not stretch or exhibit reduced stretching, while the regions which have bond lines with a cross-machine orientation will controllably stretch. The stretchability of the material is easily controlled during the bond line application process, by varying the length, thickness and density or frequency of the bond lines.

With the foregoing in mind, it is a feature and advantage of the invention to provide a stretchable nonwoven web or laminate material having bond lines to reduce or control the stretchability of the material in one or more selected directions.

It is also a feature and advantage of this invention to provide a stretchable spunbond nonwoven web or laminate material having bond lines to reduce or control the stretchability of the material in the machine direction and/or the cross-machine direction.

It is also a feature and advantage of the invention to provide a nonwoven web or laminate material having a variable stretch profile, which is useful in a wide variety of stretchable products including diapers, other personal care products, workwear and other garments.

It is also a feature and advantage of the invention to provide a variable stretch nonwoven web or laminate material having regions with cross-machine direction stretch only and regions with machine direction stretch only.

The foregoing and other features and advantages of this invention will become further apparent from the following detailed description of the preferred embodiments, read in conjunction with the drawings.

DEFINITIONS

The term "elastic" is used herein to mean any material which, upon application of a biasing force, is stretchable, that is, elongatable without rupture or breakage, to a stretched, biased length which is at least about 160 percent of its relaxed unbiased length, and which, will recover at least 55 percent of its elongation upon release of the stretching, elongating force. A hypothetical example would be a one (1) inch sample of a material which is elongatable without rupture or breakage to at least 1.60 inches and which, upon being elongated to 1.60 inches and released, will recover to a length of not more than 1.27 inches. Many elastic materials may be stretched by much more than 60 percent of their relaxed length, for example, 100 percent or more, and many of these will recover to substantially their original relaxed length, for example, to within 105 percent of their original relaxed length, upon release of the stretching force.

The term "stretchable" refers to elastic materials and other materials which exhibit the stretching properties of elastic materials without rupture or breakage, including materials that do not recover to the same extent as elastic materials.

Terms such as "more readily extensible" or "more easily extensible" mean that the force required to stretch a material in a first state, such as before bonding, is less than the force required to stretch the material to the same extent in a second state, such as after bonding.

As used herein, the term "nonelastic" refers to any material which does not fall within the definition of "elastic," above.

As used herein, the term "nonwoven web" means a web that has a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

As used herein, the term "microfibers" means small diameter fibers having an average diameter not greater than about 50 microns, for example, having a diameter of from about 0.5 microns to about 25 microns, more particularly, microfibers may have an average diameter of from about 1 micron to about 15 microns.

As used herein, the term "meltblown fibers" means fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the disclosure of which is hereby incorporated by reference.

As used herein, the term "spunbond fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbond nonwoven webs is illustrated in patents such as, for example, in U.S. Pat. No. 4,340,563 to Appel et al.; U.S. Pat. No. 3,692,618 to Dorschner et al.; and U.S. Pat. No. 3,802,817 to Matsuki et al. The disclosures of these patents are hereby incorporated by reference.

As used herein, the term "interfiber bonding" means bonding produced between individual fibers to form a coherent web structure by entanglement, adhesive bonding, or thermal bonding. Fiber entangling is normally a step in a meltblown process but may be generated or increased by processes such as, for example, hydraulic entangling or needle punching. Thermal bonding is normally a step in a spunbonding process. Alternatively and/or additionally, a bonding agent can be utilized to increase the desired bonding and to maintain structural coherency of a fibrous web. For example, powdered bonding agents and chemical solvent bonding may be used.

As used herein, the term "polymer" generally includes, but is not limited to, homopolymers, copolymers, such as for example, block, graft, random and alternating copolymers, terpolymers, etc. and blends and modifications thereof. Further, unless otherwise specifically limited, the term "polymer" shall include all possible geometrical configurations of the material. These configurations include, but are not limited to, isotactic, syndiotactic and random symmetries.

As used herein, the term "film" means a layer material formed from a cast film extrusion process, a blown film extrusion process, or another film extrusion process. The term "film" does not include nonwoven webs as defined above.

As used herein, the term "sheet" means a layer which may either be a film, foam or nonwoven web. The term "foam" means any layer which has been expanded with the aid of a foaming agent, and which includes gas-filled pockets or bubbles.

As used herein, the term "necked material" refers to any material which has been narrowed in at least one dimension by application of a tensioning force in another direction.

As used herein, the term "neckable material" means any material which can be necked.

As used herein, the term "percent neckdown" refers to the ratio determined by measuring the difference between the un-necked dimension and the necked dimension of the neckable material and then dividing that difference by the un-necked dimension of the neckable material.

As used herein, the term "stretchable laminate material" refers to a stretchable material having an elastic sheet joined to a nonwoven material. The elastic sheet may be joined to the necked material at intermittent points or may be completely bonded thereto. The joining is accomplished while the elastic sheet and the necked material are in juxtaposed configuration. The stretchable laminate material is elastic in a direction generally parallel to the direction of neckdown of the necked material. A stretchable laminate material may include more than two layers. For example, the elastic sheet may have necked material joined to both of its sides so that a three-layer stretchable laminate material is formed having a structure of necked material/elastic sheet/necked material, both necked materials being elongated in the same direction. Additional elastic sheets and/or necked material layers may be added. Yet other combinations of elastic sheets and necked materials may be used.

DETAILED DESCRIPTION OF THE PREFERRED EMBODIMENTS

In one preferred embodiment of this invention, the stretchable material having controlled stretch is an elastomeric nonwoven web. The elastomeric nonwoven web may be, for example, a spunbond web, a meltblown web, a bonded carded web, or a combination thereof. If the material is a web of meltblown fibers, it may include meltblown microfibers. The material may be made of elastomeric fiber forming polymers.

Elastic polymers suitable for use in preparing the thermoplastic elastomeric fibers herein include without limitation diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyetherester; and single-site or metallocene-catalyzed polyolefins having density less than about 0.89 grams/cc, available from Dow Chemical Co. Under the trade name AFFINITY®.

Elastomeric meltblown webs may be produced using conventional meltblowing processes and apparatus as known in the art, for example as disclosed in U.S. Pat. No. 3,849,241 to Butin et al. In meltblowing, a thermoplastic resin, here an elastomeric resin, is fed into an extruder where it is melted and heated to an appropriate temperature required for fiber formation. The extruder feeds molten resin to a special meltblowing die. The resin emerges from the die orifices as molten threads into a high velocity stream of gas, usually air. The air attenuates the polymer into a blast of fine fibers which are collected on a moving screen placed in front of the blast. As the fibers land on the screen, they entangle to form a cohesive web.

Elastomeric spunbond webs employed in this invention may be formed by techniques known in the art, for example techniques described in U.S. Pat. No. 4,340,563 to Appel et al.; U.S. Pat. No. 3,692,618 to Dorschner et al.; and U.S. Pat. No. 3,802,817 to Matsuki et al. Examples of polymers which may be suitably used to form spunbond webs include the elastomeric polymers listed above.

In accordance with this invention, the stretchability of the elastomeric nonwoven web in one or more directions and regions can be reduced or effectively eliminated by applying bond lines to the nonwoven web. A thermal calender bonding process known to those skilled in the art is used to apply the bond lines to the elastic nonwoven web. In one calendering process, the web is nipped under light pressure between a patterned steel roller which imparts the bond lines and a smooth anvil roller, with one or both rollers being heated. Other procedures may be utilized to apply bond lines to the nonwoven web including adhesive bonding and ultrasonic welding.

The bond lines applied pursuant to the invention may be in addition to any interfilament bonding that already exists from manufacture of the nonwoven web. The bond lines may be applied in a direction parallel to the cross-machine direction, or in a direction nonparallel to the cross-machine direction, preferably perpendicular to the cross-machine direction, i.e. the machine direction. The width of the nonwoven web defines the web's cross-machine direction and the length of the nonwoven web defines the machine direction of the web. The application of these bond lines to the nonwoven web results in a web comprising regions of higher extensibility having a lower level of interfilament bonding and regions of lower extensibility having a higher level of interfilament bonding corresponding to the bond lines. During the thermal calender bonding process, interfilament bonding along the bond lines is increased due to the thermal calendering. The stretchability of the nonwoven web in the cross-machine direction can be significantly reduced or effectively eliminated by applying bond lines parallel with the cross-machine direction. However, the stretchability of the nonwoven web in the cross-machine direction is not or only nominally reduced by applying bond lines in a direction nonparallel (e.g. perpendicular) to the cross-machine direction.

With the application of bond lines, an elastomeric nonwoven web may be produced that will: (a) have high extensibility in a direction in one region of the material and will have a lower extensibility in the same direction in a second region of the material; (b) stretch only in a first direction in one region of the material and stretch only in a direction nonparallel to the first direction in other regions of the material; or (c) have regions of varying extensibility in a first direction and regions of varying extensibility in a direction nonparallel to the first direction.

The elastomeric nonwoven web may be a single-layer material as described above. For example, the web may have a spunbond web having a basis weight of about 0.2–10 ounces per square yard ("osy"), or a meltblown web having a basis weight of about 0.2–8 osy. Alternatively, the elastomeric nonwoven web may be a multilayer material having, for example, at least one layer of spunbond web bonded to at least one layer of meltblown web, bonded carded web or other suitable material. For example, a material may comprise a multilayer material having a first layer of spunbond polypropylene having a basis weight from about 0.2 to about 8 osy, a layer of meltblown polypropylene having a basis weight from about 0.2 to about 4 osy, and a second layer of spunbond polypropylene having a basis weight of about 0.2 to about 8 osy.

The elastomeric nonwoven web may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

If the nonwoven web is a nonwoven web of fibers, the fibers may be joined by interfiber bonding to form a coherent web structure. Interfiber bonding may be produced by thermal bonding in a spunbonding process, or entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding.

In another preferred embodiment of this invention, the material having controlled stretching can be a stretchable laminate material comprising an elastic film and a neckable web. One process for forming a stretchable laminate material is disclosed in U.S. Pat. No. 5,883,028 issued to Morman et al., the disclosure of which is hereby incorporated by reference.

In the process disclosed in Morman et al., a neckable web, preferably a neckable spunbond web, passes through a S-roll arrangement where the neckable web can be tensioned in the machine direction to neck a desired amount in the cross-machine direction, and is maintained in such tensioned, necked condition while an elastic film or sheet is bonded to the necked web to form a stretchable laminate material. The nonwoven web itself need not be elastic. The bonding of the necked web to an elastic film produces an elastic laminate which is stretchable in a direction parallel to the direction of necking.

Other methods of tensioning the neckable web may be used such as, for example, tenter frames or other cross-machine direction tensioning arrangements that expand the neckable web in other directions such as, for example, the cross-machine direction so that, after bonding to the elastic sheet, the resulting stretchable laminate material will be elastic in a direction generally parallel to the direction of necking, i.e. in the machine direction.

The neckable web may be a porous nonwoven material such as, for example, spunbond web, meltblown web or bonded carded web or a combination thereof. If the neckable material is a web of meltblown fibers, it may include meltblown microfibers. The neckable nonwoven web may be inelastic. The neckable material may be made of fiber forming polymers such as, for example, one or more polyolefins. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation Exxon 3445, and polypropylene available from the Shell Chemical Company under the trade designation DX 5A09.

The neckable web may be a single layer of material such as, for example, a spunbond web having a basis weight of from about 0.2 to about 10 osy or a meltblown web having a basis weight of from about 0.2 to about 8 osy. Alternatively, the neckable web may be a multilayer material having, for example, at least one layer of spunbond web bonded to at least one layer of meltblown web, bonded carded web or other suitable material. For example, a neckable material may comprise a multilayer material having a first layer of spunbond polypropylene having a basis weight from about 0.2 to about 8 ounces per square yard (osy), a layer of meltblown polypropylene having a basis weight from about 0.2 to about 4 osy, and a second layer of spunbond polypropylene having a basis weight of about 0.2 to about 8 osy.

The neckable material may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324.

If the neckable web is a nonwoven web of fibers, the fibers should be joined by interfiber bonding to form a coherent web structure which is able to withstand necking. Interfiber bonding may be produced by thermal bonding in a spunbonding process, or by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding.

The elastic sheet may be a single layer or multilayer material, including one or more individual coherent webs, films and/or foams. Additionally, the elastic sheet may be a single layer or multilayer material in which one or more of the layers contain a mixture of elastic and nonelastic fibers or particulates. The elastic sheet may be formed from one or more of the elastic polymers listed above.

Elastic sheets can be used having basis weights less than 0.5 osy (ounces per square yard), for example, from about 0.25 to about 0.4 osy. Such extremely low basis weight sheets are advantageous because of higher breathability and economic reasons, and are particularly useful in disposable products. Additionally, elastic sheets having higher basis weights such as, for example, from about 0.5 to about 10 osy, or about 11 to about 40 osy, may also be used.

Necked materials may be joined to the elastic sheet by any suitable means such as, for example, thermal or adhesive bonding or ultrasonic welding which softens at least portions of at least one of the materials, usually the elastic sheet because the elastomeric materials used for forming the elastic sheet have a lower softening point than the components of the necked material. The necked material and the elastic sheet may be completely bonded together and still provide a stretchable laminate material with good stretch properties. Joining may be produced by applying heat and/or pressure to the overlaid elastic sheet and the necked material by heating these portions (or the overlaid layer) to at least the softening temperature of the material with the lowest softening temperature to form a reasonably strong and permanent bond between the re-solidified softened portions of the elastic sheet and the necked material. Conditions should not be so severe as to perforate the film. Suitable bonding conditions are described in the above-mentioned U.S. Pat. No. 5,883,028 to Morman et al.

The relation between the original dimensions of the neckable material to its dimensions after tensioning determines the initial limits of stretch of the stretchable laminate material, i.e. before the bonding lines are applied pursuant to this invention. Because the neckable material is able to stretch and return to its necked dimensions in directions such as, for example the machine direction or the cross-machine direction, the laminate material will be stretchable in generally the same direction as the neckable material.

In another neck-bonded laminate, the elastic sheet (i.e. film, foam or web) may be stretched in a direction other than parallel (e.g., perpendicular) to the direction of necking of the nonwoven web, and laminated to the neckable nonwoven web in a plurality of spaced apart locations while the sheet is in the stretched condition and while the web is necked. After lamination, the elastic sheet is relaxed, causing puckering or gathering of the web between the bonded regions. The resulting composite laminate is initially stretchable in at least two nonparallel directions. The stretchability of the composite in the directions parallel to the direction of necking is facilitated by the necking of the web. The stretchability of composite in the direction nonparallel (e.g., perpendicular) to the direction of necking is facilitated by the gathering of the web in that direction. Processes for making a multidirectional stretchable laminate from an elastic sheet and necked nonwoven web are described in U.S. Pat. Nos. 5,116,662 and 5,114,781, both issued to Morman, the disclosures of which are incorporated herein by reference.

Using an unnecked nonwoven web for the above-described process would produce a laminate that stretches only in the direction that the elastic sheet was stretched prior to bonding. Such a process, and a resulting laminate, are described in U.S. Pat. No. 4,720,415, issued to Vander Wielen et al.

Other layer combinations are also possible for controlled stretch laminates of this invention. For these aspects of the invention, the laminate material should include at least one elastic sheet and at least one necked or un-necked nonwoven (preferably spunbond) layer. In one embodiment, a reversibly necked nonwoven web may be laminated to an elastic film, as described in U.S. Pat. No. 5,114,781 issued to Morman.

In accordance with this invention, a stretchable laminate material comprising an elastic sheet (i.e. film, foam or web) and a neckable nonwoven web can be produced by the bonding process disclosed above. The stretchability of the stretchable laminate material can be reduced or effectively eliminated in one or more regions and directions by selectively applying bond lines to the laminate, preferably after the web is necked and bonded to the elastic sheet to form the stretchable laminate material. The applied bond lines impart additional localized interfilament and interlayer bonding, beyond that which already exists from manufacture of the neckable web and laminate.

In the preferred embodiment of this invention, a thermal calender bonding process known to those skilled in the art is used to apply the bond lines to the laminate material. Other procedures may be utilized to apply bond lines to the laminate, including other thermal bonding, adhesive bonding and ultrasonic welding. These bond lines may be applied in a direction parallel to the direction of necking, i.e. the cross-machine direction, or in a direction nonparallel to the direction of necking, preferably perpendicular to the direction of necking, i.e. the machine direction. The width of the laminate material defines the material's cross-machine direction and the length of the laminate material defines the machine direction of the material.

The application of these bond lines to the laminate material results in a laminate material comprising regions of higher extensibility having a lower level of interfilament bonding and regions of lower extensibility having a higher level of interfilament bonding corresponding to the bond lines. The stretchability of the laminate material in the cross-machine direction, for instance, can be significantly reduced or effectively eliminated by applying bond lines parallel with the cross-machine direction. However, the stretchability of the laminate material in the cross-machine direction is not or only nominally reduced by applying bond lines in a direction nonparallel (e.g. perpendicular) to the cross-machine direction.

With the application of bond lines, a material may be produced that will: (a) have high extensibility in a direction in one region of the material and will have a lower extensibility in the same direction in a second region of the material; (b) readily or easily stretch only in a first direction in one region of the material and readily or easily stretch only in a direction nonparallel to the first direction in other regions of the material; or (c) have regions of varying extensibility in a first direction and regions of varying extensibility in a direction nonparallel to the first direction.

FIGS. 1–3(b) of the drawings illustrate an exemplary region 10 of a stretchable nonwoven web or laminate material and the effect on stretchability in the cross-machine direction when a series or plurality of bond lines 11 are applied to region 10 of the nonwoven web or laminate material using, for instance, a thermal calender bonding process. Referring to FIG. 1(a), when a tensioning force is applied in the cross-machine direction to region 10 of the stretchable nonwoven web or laminate material without bond lines, the material is highly stretchable and stretches in one direction (the machine direction or cross-machine direction) to the dimension shown in FIG. 1(b).

Figure 1A:
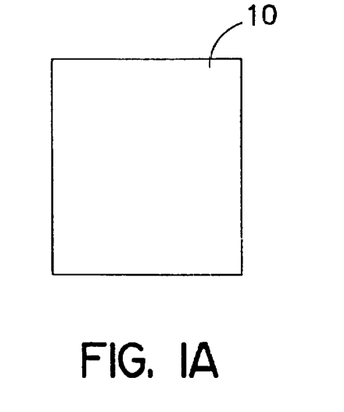
FIG. 1(a) is a plan view of an exemplary stretchable nonwoven web or laminate material without bond lines.
Figure 1B:
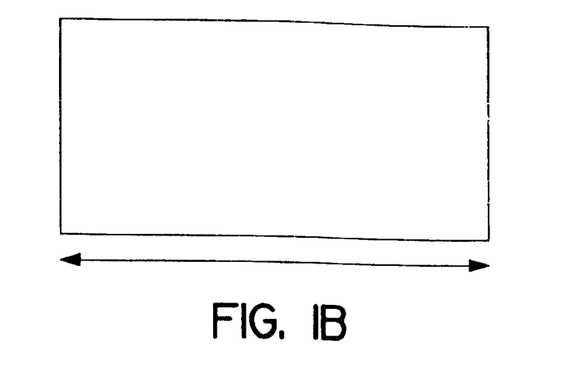
FIG. 1(b) is a plan view of the exemplary stretchable nonwoven web or laminate material of FIG. 1(a) showing the stretchability in one direction, such as the cross-machine direction, when bond lines are not present.
Figure 2A:
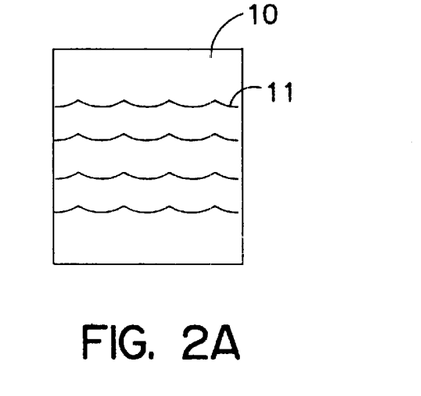
FIG. 2(a) is a plan view of an exemplary stretchable nonwoven web or laminate material with bond lines applied in one direction, such as the cross-machine direction.
Figure 2B:
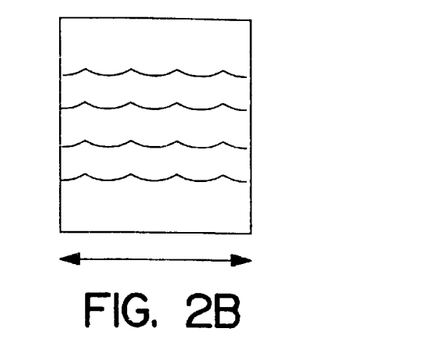
FIG. 2(b) is a plan view of the exemplary stretchable nonwoven web or laminate material of FIG. 2(a) showing the reduction in stretchability in the cross-machine direction when bond lines are applied in the cross-machine direction.

FIG. 2(a) shows a plan view of an exemplary region 10 of an otherwise similar stretchable nonwoven web or laminate material with a series of continuous bond lines 11 applied to region 10 in the same direction, for instance, in a direction parallel to the direction of necking in a neck-bonded laminate material. The application of one or a series of bond lines 11 parallel to a direction of stretch in region 10 significantly decreases or eliminates the stretchability of the material in region 10 in that direction, as shown in FIG. 2(b). The level of extensibility along the bond lines 11 is significantly decreased due to the increased interfilament bonding, attachment and/or densification of the web or laminate material caused by the thermal calender bonding process. As shown in FIG. 2(b), when a tensioning force is applied to the material in a direction parallel to bond lines 11 (e.g. a cross-machine direction in a neck-bonded laminate, or any direction in an elastomeric nonwoven web) the material in region 10 will not stretch or only stretch a nominal distance.

Figure 3A:
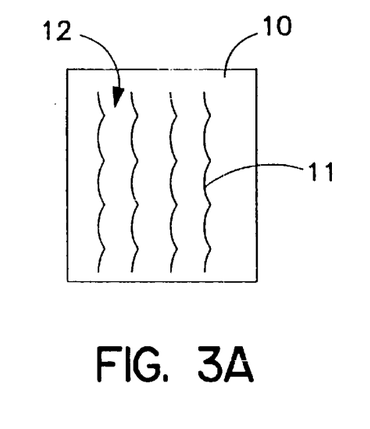
FIG. 3(a) is a plan view of an exemplary stretchable nonwoven web or laminate material with bond lines applied in another direction, such as the machine direction.
Figure 3B:
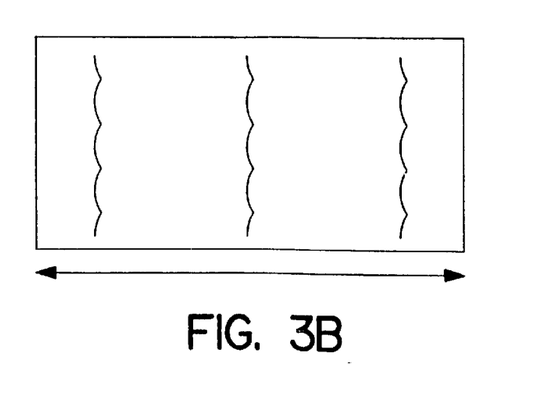
FIG. 3(b) is a plan view of the exemplary stretchable nonwoven web or laminate material of FIG. 3(a) showing some reduction (but not elimination) in stretchability in the cross-machine direction when bond lines are applied in the machine direction.

FIG. 3(a) shows a plan view of an exemplary region 10 of a stretchable nonwoven web or laminate material with a series of continuous bond lines 11 applied to region 10 perpendicular to a direction of stretch (e.g. a machine direction in a neck-bonded laminate or any direction in an elastomeric nonwoven web). When one or a series of bond lines 11 is applied perpendicular to a direction of stretch in region 10 of the nonwoven web or laminate material, the stretchability of the material in the direction of stretch is only nominally affected. As shown in FIG. 3(b), when a tensioning force is applied to the material in the direction of stretch, the bond lines 11 have only a nominal effect on the distance the material in region 10 is able to be stretched. Because the bond lines 11 are nonparallel to the direction of the tensioning force, the increased interfilament bonding and densification along the bond lines 11 due to the thermal calender bonding process has little or no effect on the ability of regions of higher extensibility 12 (between the bond lines) to stretch in the desired direction.

Figure 4A:
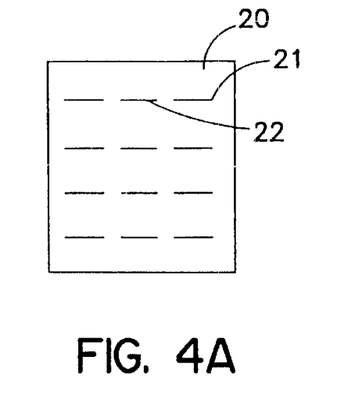
FIG. 4(a) is a plan view of an exemplary stretchable nonwoven web or laminate material with variable bond lines applied to the material in the cross-machine direction, occupying 50% of the material width.

The reduction in stretchability which results from applying bond lines 11 to region 10 of the nonwoven web or laminate material can easily be controlled and varied. The continuous bond lines 11 as shown in FIGS. 2 and 3 can be separated into a plurality of noncontinuous bond line segments 22 as shown in FIG. 4(a) to form dashed, noncontinuous bond lines 21. The length of the individual bond line segments 22, the number of bond line segments 22 comprising a noncontinuous bond line 21, and the distance between them affect the stretchability of the material in region 20. In one preferred embodiment of this invention, the bond line segments 22 that comprise noncontinuous bond line 21 are of about equal length and spacing. However, in other preferred embodiments of this invention, bond line segments 22 may be of nonuniform lengths and/or spacing to effect nonuniform stretching. Further, in one preferred embodiment of this invention, successive noncontinuous bond lines 21 may be comprised of bond line segments 22 of about equal lengths and spacing, or each successive bond line 21 may comprise bond line segments 22 of varying uniform or nonuniform lengths and/or spacing.

Figure 4B:
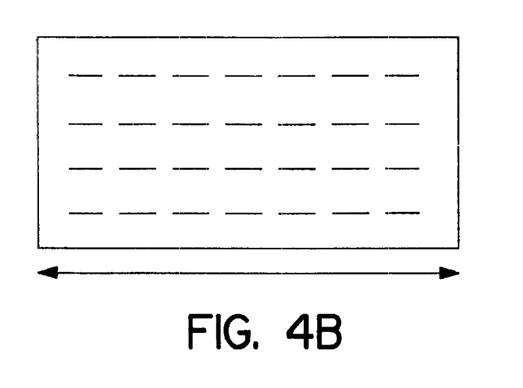
FIG. 4(b) is a plan view of the exemplary stretchable nonwoven web or laminate material of FIG. 4(a) showing the reduction in stretchability in the cross-machine direction when variable bond lines are applied to the material in the cross-machine direction, occupying 50% of the material width. Most of the stretching occurs in the spaces between the bond lines.
Figure 5A:
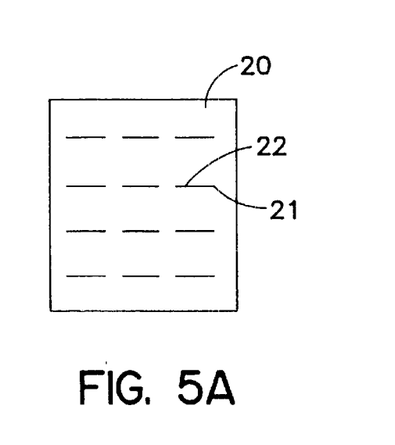
FIG. 5(a) is a plan view of an exemplary stretchable nonwoven web or laminate material with variable bond lines applied to the material in the cross-machine direction, occupying 75% of the material width.
Figure 5B:
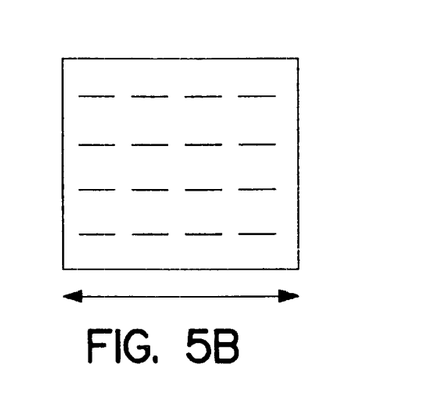
FIG. 5(b) is a plan view of the exemplary stretchable nonwoven web or laminate material of FIG. 5(a) showing the greater reduction in stretchability in the cross-machine direction when variable bond lines are applied to the material in the cross-machine direction, occupying 75% of the material width. Again, most of the stretching occurs in the spaces between the bond lines.
Figure 6A:
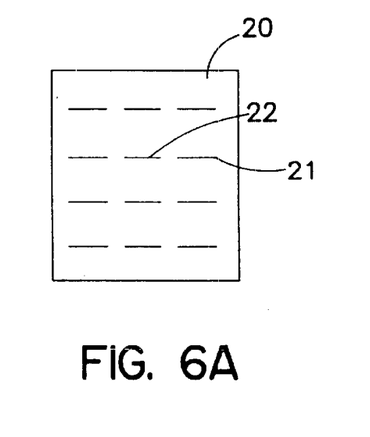
FIG. 6(a) is a plan view of an exemplary stretchable nonwoven web or laminate material having variable bonding.
Figure 6B:
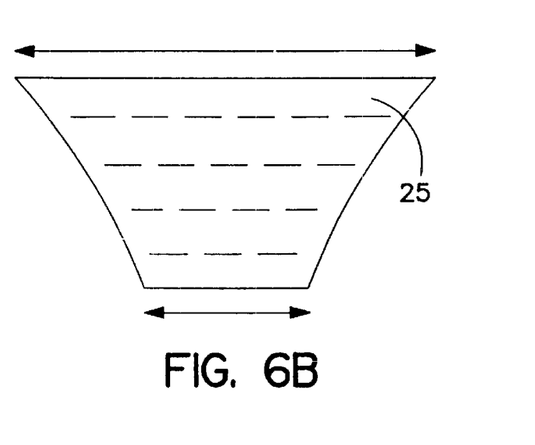
FIG. 6(b) is a plan view of the exemplary stretchable nonwoven web or laminate material of FIG. 6(a) having variable bonding, showing the variable stretch profile when variable bonding is employed.

FIGS. 4–6 show a plan view of an exemplary region 20 of a stretchable nonwoven web or laminate material showing the effects of noncontinuous bond lines 22 on the stretchability of a material in a direction parallel with the bond lines 22.

The Reduction in Stretchability ($R_S$) of the nonwoven web or laminate material in region 20 when bond lines 21 are applied can be represented as follows:

$$R_S = f(W_b, S_i);$$

where $W_b$ represents the fraction of material width occupied by a bond line 21 and $S_i$ represents the initial stretchability of the material in the direction of stretching. This means that $R_s$ is a function of $W_b$ and $S_i$. If the stretchability is zero at the precise location of a bond line 21, then $R_s$ is at its maximum value of 1.0.

FIGS. 4(a) and 4(b) show a plan view of an exemplary region 20 of a stretchable nonwoven web or laminate material and the reduction in stretchability exhibited by region 20 when a tensioning force is applied to the material in the cross-machine direction. The illustrated region 20 of a stretchable nonwoven web or laminate material has an initial stretchability (without bond lines) of 200% in the direction of stretch, e.g. the cross-machine direction. Assuming $R_s$ is directly proportional to the function of material bonded, as in an ideal situation, a series of noncontinuous bond lines 21 occupying six-tenths of the material width in the cross-machine direction will reduce the stretch of the material in region 20 by about six-tenths, from 200% to 80%, when a tensioning force is applied, i.e. $R_S = 0.60 * 200\% = 120\%$.

Similarly, FIG. 5(a) shows a region 20 of a stretchable nonwoven web or laminate material having an initial stretchability of 200% in the direction of stretch, e.g. the cross-machine direction. Assuming ideally, a series of noncontinuous bond lines 21 occupying three-quarters of the material width in that direction, will reduce the stretch of the material by three-quarters to about 50% when a tensioning force is applied, i.e. $R_S=0.75*200\%=150\%$.

As shown in FIGS. 6(a) and 6(b), a bonding strategy can be employed whereby the percentage of a material's length or width occupied by each noncontinuous bond line 21 varies with successive noncontinuous bond lines 21. This variation in size and spacing of segments 22 for successive bond lines 21, produces a region 20 of a material with a variable stretch profile 25 as shown in FIG. 6(b). As a result of this variable bonding, the material will stretch to different lengths along successive bond lines 21 when a tensioning force is applied to the material in a direction parallel to the bond line orientation. The percentage of a material's length or width occupied by a noncontinuous bond line 21 is controlled by the number of bond line segments 22, by the length of the individual bond line segments 22, and by the spacing between segments 22 in each noncontinuous bond line 21. The reduction in stretchability along each noncontinuous bond line 21 can be estimated using the equation above. Bond lines 21 can be applied to region 20 in a predetermined pattern to produce a nonwoven web or laminate material with various stretch profiles 25.

In another preferred embodiment of this invention, a biaxially stretchable elastic nonwoven web, or a necked stretched bonded nonwoven laminate (NSBL) material comprising a stretched elastic sheet thermally bonded to a necked nonwoven (e.g. spunbond) web is produced by a procedure discussed above. The elastic nonwoven web, or the necked stretched bonded laminate material, is capable of stretching in all directions. Bond lines can be applied by the thermal calender bonding process discussed above, or by another process, to produce a material having regions wherein bond lines are applied in a direction parallel to the cross-machine direction and having regions wherein bond lines are applied in a direction nonparallel to the cross-machine direction, preferably perpendicular to the cross-machine direction, i.e. in the machine direction. The stretchability in either the cross-machine direction or the machine direction of a region of the material is reduced or effectively eliminated by applying bond lines to that region. The bond lines may be continuous or noncontinuous. Further, bond lines can be applied in a region of the material to profile the machine direction stretch and/or the cross-machine direction stretch in that region of the material.

Figure 7A:
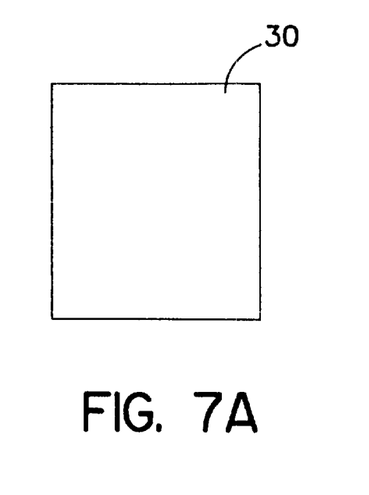
FIG. 7(a) is a plan view of an exemplary stretchable spunbond nonwoven web or laminate material with no bond lines present.
Figure 7B:
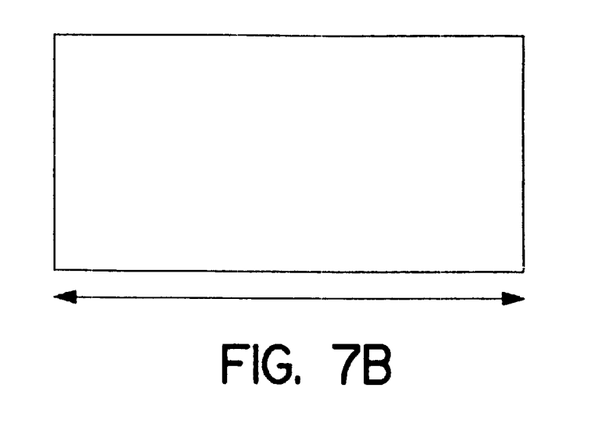
FIG. 7(b) is a plan view of the stretchable spunbond nonwoven web or laminate material of FIG. 7(a), showing the stretchability of the material in the machine direction when bond lines are not present.
Figure 7C:
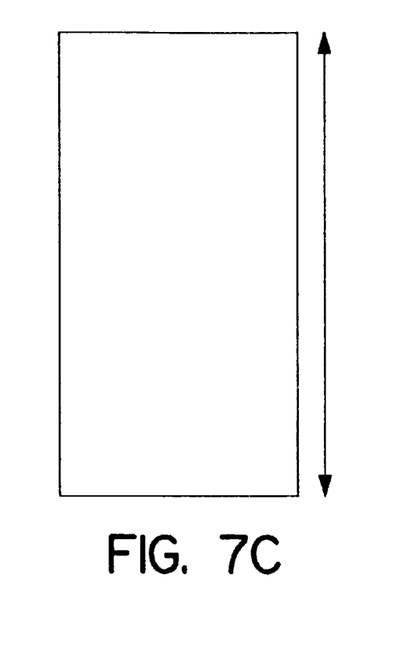
FIG. 7(c) is a plan view of the stretchable spunbond nonwoven web or laminate material of FIG. 7(a), showing the stretchability of the material in the cross-machine direction when bond lines are not present.

FIG. 7(a) illustrates a section 30 of an elastic spunbond nonwoven web or elastic NSBL material with no bond lines. This material can be stretched in the machine direction (See FIG. 7(b)) and the cross-machine direction (See FIG. 7(c)).

Figure 8A:
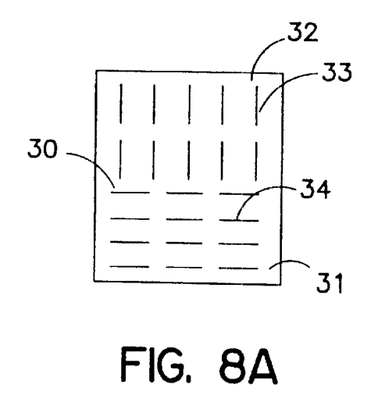
FIG. 8(a) is a plan view of the stretchable spunbond nonwoven web or laminate material of FIG. 7(a), with bond lines applied to the material in the machine direction in a first region of the material and in the cross-machine direction in a second region of the material.
Figure 8B:
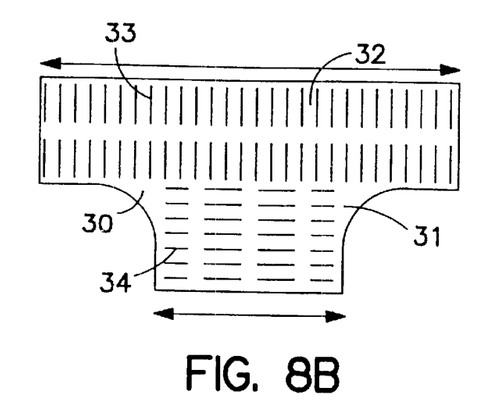
FIG. 8(b) is a plan view of the stretchable spunbond nonwoven web or laminate material of FIG. 8(a), showing the effects on stretchability of the material in the machine direction when bond lines are applied to the material in the machine direction in a first region of the material and in the cross-machine direction in a second region of the material.
Figure 8C:
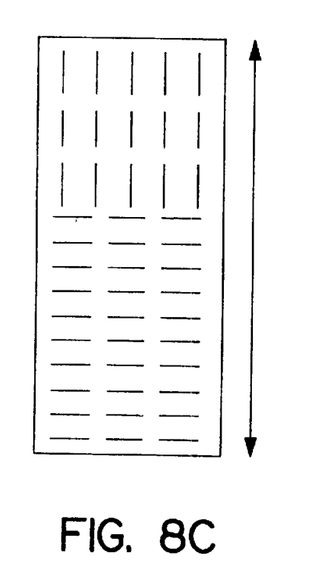
FIG. 8(c) is a plan view of the stretchable spunbond nonwoven web or laminate material of FIG. 8(a), showing the effects on stretchability of the material in the cross-machine direction when bond lines are applied to the material in the machine direction in a first region of the material and in the cross-machine direction in a second region of the material.

As shown in FIGS. 8(a)–8(c), when bond lines 33, 34 are applied to regions 31, 32 of section 30 of a stretchable nonwoven web or NSBL material, the material exhibits zoned stretching. Bond lines 33 are applied in the machine direction in an upper region 32. Bond lines 34 are in the cross-machine direction in a lower region 31. FIG. 8(b) shows a section 30 of an elastic nonwoven web or necked spunbond laminate material exhibiting zoned stretching. As shown in FIG. 8(b), when a tensioning force is applied in the cross-machine direction to the material, region 31, in which the bond lines 34 are parallel with the direction of the force, stretches to a lesser extent. Region 32 in which bond lines 33 are nonparallel, preferably perpendicular, to the direction of the tensioning force stretches to a greater extent. Conversely, as shown in FIG. 8(c), when a tensioning force is applied in the machine direction to the material, region 32 in which bond lines 33 are parallel to the direction of the tensioning force stretches to a lesser extent, while region 31 in which bond lines 34 are nonparallel, preferably perpendicular, to the direction of the tensioning force stretches to a greater extent.

The bond lines which are used to effect the controlled stretching are distinguishable from the interfilament bond patterns already existing in a nonwoven web, and from the inter-layer bonding in a laminate. Typically, the bond lines used to effect controlled stretching are relatively long and narrow, and substantially straight (i.e. directionally oriented). The individual bond line segments (if the lines are discontinuous) typically have a length of at least 0.1 inch, preferably at least about 0.2 inch, more preferably at least about 0.3 inch. If an individual bond line is segmented, the segments are substantially aligned. The overall bond line length (i.e. the sum total of aligned segment length, or total line length, if not segmented) is typically at least about 0.5 inch, preferably at least about 1.0 inch, more preferably at least about 1.5 inch. The bond line segments have greater lengths than widths. Typically, a bond line segment has a length/width ratio (L/D) of at least 2.0, preferably at least 3.0, more preferably at least 4.0. Typically, the L/D of the overall bond lines (i.e. based on the sum of the segment lengths, or the total bond length if continuous) is at least about 10, preferably at least about 15, more preferably at least about 20. The spacing between adjacent (e.g. parallel) bond lines can also be varied and is generally at least about 0.1 inch, preferably at least about 0.2 inch, more preferably at least about 0.3 inch.

The spunbond bond sites (imparted during manufacture of the web) are in place before necking the spunbond web, and allow it to neck. Without these bond sites, the material would pull apart. These bond sites are uniformly spaced, and do not selectively inhibit stretching. Further bonding filaments in accordance with the invention when the spunbond is necked, inhibits the stretching in the cross-machine direction.

EXAMPLES

The following examples further illustrate the invention.

Example 1

A nonwoven meltblown web having a basis weight of 72 grams per square meter (gsm) was formed from 60% by weight KRATON® G1657, which is a styrene/ethylene-butylene/styrene block copolymer available from the Shell Chemical Co., and 40% by weight low density polyethylene. A sample measuring about 5 inches wide and 10 inches long (including first and second 5-inch by 5-inch areas) was cut and used for testing. The sample was initially readily and easily stretchable in all directions.

Three one-inch wide and 4.5-inches long strips of 3M Transfer Tape, made by the Minnesota Mining & Mfg. Co., were placed parallel to each other and about 0.75-inch apart from each other in the first area, in about the machine direction of the meltblown web. Three similar strips were placed parallel to each other and about 0.75-inch apart from each other in the second area, in about the cross-machine direction of the melt-blown web. The release paper was removed from all six strips, leaving only adhesive lines on the meltblown web. Baby powder from the Johnson & Johnson Co. was dusted over the exposed adhesive strips to facilitate handling of the treated meltblown web.

The resulting material has reduced machine direction stretch in the first area (having machine direction oriented strips) and reduced cross direction stretch in the second area (having cross direction-oriented strips).

Example 2

A piece of 6-inch wide, 10-inch long SBL (stretch-bonded laminate) was provided based on the disclosure of U.S. Pat. No. 4,720,415, which is incorporated by reference. The SBL had two outer polypropylene spunbond layers with basis weights of 29 gsm each, and an inner meltblown layer made from the above-described blend of KRATON® G1657 and polyethylene, having a basis weight of 72 gsm. An edge of the SBL sample, measuring about 1.375 inches wide, was placed in a platen press, Model 0230C-X1-4B-7, made by PHI Inc. of City Of Industry, Cal. The press had a 5-inch diameter ram. The remaining width of the sample, measuring about 4.625 inches, was not placed in the press.

The press platens were set to 110° F., giving actual readings of 118° F. for the top platen and 111° F. for the bottom platen. The press was closed over the sample edge for 2 minutes at a ram pressure of 15 tons. After releasing the press, the pressed edge of the SBL would not readily stretch in the machine direction of the spunbond webs, while the portion of the SBL not pressed readily stretched in the machine direction.

Example 3

A piece of 6-inch wide, 6-inch long NBL (neck-bonded laminate) was provided based on the disclosure of U.S. Pat. No. 5,336,545, which is incorporated by reference. The NBL had two outer polypropylene spunbond layers, and an inner film layer of the KRATON® G1657 blended with polyethylene, as described above, and with a REGALREZ® tackifier as described in U.S. Pat. No. 4,789,699 to Kieffer et al., incorporated by reference. An edge of the sample, measuring one inch in width, was placed in the platen press described in Example 2. The direction of stretch was perpendicular to the one-inch width. The press platens were set at 110° F., and had actual readings of 115° F. for the top platen and 111° F. for the bottom platen. The edge was pressed for two minutes using a ram pressure of 15 tons.

After releasing the press, the NBL would not readily stretch in the pressed area, and readily stretched in the remaining area that was not pressed.

Example 4

A piece of 6-inch wide, 12-inch long reversibly necked spunbond polypropylene was produced based on the disclosure of U.S. Pat. No. 4,965,122, which is incorporated by reference. One edge of the material, measuring one inch in width, was pressed at 15 tons ram pressure for two minutes at 250° F. platen settings using the same press as in Examples 3 and 4. The sample had good stretch in the non-compressed region and only slight resistance to stretch in the compressed region.

Using an identical material sample, the experiment was repeated using platen settings of 275° F. (giving actual readings of 289° F. for the top platen and 287° F. for the bottom platen). The uncompressed region had good stretch, while the compressed region exhibited high resistance to stretching.

It is to be understood that variations and modifications of the present invention may be made without departing from the scope of the present invention. It is also to be understood that the scope of the present invention is not to be interpreted as limited to the specific embodiments disclosed herein. The scope of the invention is indicated in the appended claims, and all changes that fall within the meaning and range of equivalents are intended to be embraced therein.

We claim:

1. A stretchable laminate material comprising:

an elastic sheet; and a nonwoven web bonded to said elastic sheet when the web is necked in a first direction;

the laminate material having a plurality of bond lines oriented in a direction selected from the first direction and a second direction nonparallel to the first direction;

wherein the bond lines comprise segments having a bond line segment length of at least about 0.3 inch and a length/width ratio of at least about 3.

2. The stretchable laminate material of claim 1, wherein said laminate material has a variable stretch profile in the first direction.

3. The stretchable laminate material of claim 1, wherein said nonwoven web comprises a material selected from the group consisting of spunbond webs, meltblown webs, carded webs, and combinations thereof.

4. The stretchable laminate material of claim 1, wherein the bond line segments of different bond lines cover varying percentages of the laminate material in the first direction.

5. The stretchable laminate material of claim 1, wherein the elastic sheet is bonded to the nonwoven web by adhesive bonding.

6. The stretchable laminate material of claim 1, wherein said bond lines are oriented in the first direction.

7. The stretchable laminate material of claim 1, wherein the bond lines are oriented in the second direction nonparallel to the first direction.

8. A personal care product comprising the stretchable laminate material of claim 1.

9. The personal care product of claim 8, comprising a diaper.

10. A garment comprising the stretchable laminate material of claim 1.

11. The stretchable laminate material of claim 1, wherein the bond lines have a bond line length of at least about 1.0 inch.

12. The stretchable laminate material of claim 1, wherein the bond lines have a bond line length of at least about 1.5 inch.

13. The stretchable laminate material of claim 1, wherein the spacing between parallel bond lines is at least about 0.2 inch.

14. The stretchable laminate material of claim 1, wherein the spacing between parallel bond lines is at least about 0.3 inch.

15. The stretchable laminate material of claim 1, wherein the bond lines have a length/width ratio of at least about 10.

16. The stretchable laminate material of claim 1, wherein the bond lines have a length/width ratio of at least about 15.

17. The stretchable laminate material of claim 1, wherein the bond lines have a length/width ratio of at least about 20.

18. A necked stretched bonded laminate material comprising:

a necked spunbond web having a machine direction and a cross-machine direction, the necked spunbond web bonded to an elastic sheet;

the laminate material further comprising at least one first region having a plurality of bond lines oriented in a direction substantially parallel to said machine direction, and at least one second region having a plurality of bond lines oriented in a direction substantially parallel to said cross-machine direction;

wherein the bond lines comprise segments having a length of at least about 0.3 inch and a length/width ratio of at least about 3.

19. The necked stretched bonded laminate material of claim 18, wherein the first region is adjacent to the second region.

20. The necked stretched bonded laminate material of claim 18, wherein said first region is stretchable primarily in the cross-machine direction and said second region is stretchable primarily in the machine direction.

21. A personal care product comprising the necked stretch bonded laminate material of claim 18.

22. The personal care product of claim 21, comprising a diaper.

23. A garment comprising the necked stretch bonded laminate material of claim 18.

* * * * *